(12) United States Patent
Zucker et al.

(10) Patent No.: US 11,847,809 B2
(45) Date of Patent: Dec. 19, 2023

(54) SYSTEMS, DEVICES, AND METHODS FOR IDENTIFYING AND LOCATING A REGION OF INTEREST

(71) Applicant: Mazor Robotics Ltd., Caesarea (IL)

(72) Inventors: Ido Zucker, Tel Aviv (IL); Avi Turgeman, Beer Yaakov (IL)

(73) Assignee: Mazor Robotics Ltd., Caesarea (IL)

( * ) Notice: Subject to any disclaimer, the term of this patent is extended or adjusted under 35 U.S.C. 154(b) by 312 days.

(21) Appl. No.: 17/373,541

(22) Filed: Jul. 12, 2021

(65) Prior Publication Data

US 2023/0012440 A1 Jan. 12, 2023

(51) Int. Cl.
| | |
|---|---|
| *A61B 34/20* | (2016.01) |
| *G06T 7/73* | (2017.01) |
| *G06V 10/25* | (2022.01) |
| *A61B 34/30* | (2016.01) |
| *G06T 7/246* | (2017.01) |
| *A61B 90/00* | (2016.01) |

(52) U.S. Cl.
CPC ............ *G06V 10/25* (2022.01); *A61B 34/20* (2016.02); *A61B 34/30* (2016.02); *G06T 7/246* (2017.01); *G06T 7/73* (2017.01); *A61B 2034/2057* (2016.02); *A61B 2034/2065* (2016.02); *A61B 2090/363* (2016.02); *G06T 2207/10028* (2013.01); *G06T 2207/30012* (2013.01); *G06T 2207/30196* (2013.01); *G06T 2207/30204* (2013.01); *G06V 2201/033* (2022.01)

(58) Field of Classification Search
CPC ......... G06T 7/0012; G06T 7/246; G06T 7/70; G06T 7/73; G06T 2207/30008; G06T 2207/30012; G06T 2207/30196; G06V 10/25; G06V 2201/033; A61B 34/20; A61B 2034/2055; A61B 2034/2057; A61B 2034/2065
See application file for complete search history.

(56) References Cited

U.S. PATENT DOCUMENTS

| | | | |
|---|---|---|---|
| 6,514,219 B1 * | 2/2003 | Guimond et al. ... | A61B 5/1127 600/595 |
| 10,595,941 B2 | 3/2020 | Herrmann et al. | |

(Continued)

FOREIGN PATENT DOCUMENTS

| | | |
|---|---|---|
| WO | WO 2018/049196 A1 | 3/2018 |
| WO | WO 2018/075784 A1 | 4/2018 |

OTHER PUBLICATIONS

International Search Report and Written Opinion for International (PCT) Patent Application No. PCT/IL2022/050736, dated Jan. 3, 2023, 20 pages.

*Primary Examiner* — Andrew W Johns
(74) *Attorney, Agent, or Firm* — Sheridan Ross P.C.

(57) ABSTRACT

Systems, devices, and methods for identifying a region of interest are provided. A plurality of skeletal landmarks may be identified from an image received from an imaging device. A pose of a patient may be determined based on the plurality of skeletal landmarks. A region of interest may be identified on the patient based on the determined pose. Instructions may be automatically provided to the controller to adjust a pose of a surgical instrument relative to the region of interest. The plurality of skeletal landmarks may be tracked for movement. The region of interest may be updated when movement of the plurality of skeletal landmarks is detected.

9 Claims, 5 Drawing Sheets

(56) References Cited

U.S. PATENT DOCUMENTS

| | | |
|---|---|---|
| 10,602,114 B2 | 3/2020 | Casas |
| 2002/0077543 A1* | 6/2002 | Grzeszczuk et al. .. A61B 90/36 348/E13.008 |
| 2010/0128953 A1* | 5/2010 | Ostrovsky-Berman ...................... G06T 7/35 382/131 |
| 2023/0215096 A1* | 7/2023 | Hall .......................... G06T 7/55 345/419 |

* cited by examiner

SYSTEMS, DEVICES, AND METHODS FOR IDENTIFYING AND LOCATING A REGION OF INTEREST

FIELD

The present technology generally relates to identifying a region of interest and relates more particularly to using imaging to identify and locate the region of interest.

BACKGROUND

Imaging may be used by a medical provider for diagnostic and/or therapeutic purposes. Surgical robots may assist a surgeon or other medical provider in carrying out a surgical procedure or may complete one or more surgical procedures autonomously. The surgical robots and imaging may be jointly used to carry out the surgical procedure.

SUMMARY

Example aspects of the present disclosure include:

A system for identifying a region of interest according to at least one embodiment of the present disclosure comprises an imaging device; a controller; at least one processor; and a memory storing data for processing by the processor, the data, when processed, causing the processor to: identify a plurality of skeletal landmarks from an image received from the imaging device; determine a pose of a patient based on the plurality of skeletal landmarks; identify a region of interest on the patient based on the determined pose; automatically provide instructions to the controller to adjust a pose of a surgical instrument relative to the region of interest; track the plurality of skeletal landmarks for movement; and update the region of interest when movement of the plurality of skeletal landmarks is detected.

Any of the aspects herein, wherein the imaging device comprises a depth camera.

Any of the aspects herein, wherein the memory stores further data for processing by the processor that, when processed, causes the processor to automatically provide updated instructions to the controller that adjusts the pose of the surgical instrument relative to the updated region of interest.

Any of the aspects herein, wherein the region of interest comprises a spinal region.

Any of the aspects herein, wherein the region of interest is identified relative to the plurality of skeletal landmarks.

Any of the aspects herein, wherein the surgical instrument comprises at least one robotic arm.

Any of the aspects herein, further comprising a table on which the patient is positioned, and wherein the memory stores further data for processing by the processor that, when processed, causes the processor to cause the table to position the patient and orient the at least one robotic arm based on the region of interest.

Any of the aspects herein, wherein the at least one robotic arm and the table operate in a common coordinate space.

Any of the aspects herein, wherein the region of interest is a first region of interest, and wherein the memory stores further data for processing by the processor that, when processed, causes the processor to: identify a second region of interest, wherein the first region of interest is identified at a time stamp prior to a time stamp of the second region of interest, and the first region of interest has a pose different from a pose of the second region of interest.

A device for identifying a region of interest according to at least one embodiment of the present disclosure comprises at least one processor; and a memory storing data for processing by the processor, the data, when processed, causing the processor to: receive an image, the image depicting a patient; input the image to a region of interest model, wherein the region of interest model is trained using historical data, and wherein the region of interest model is configured to identify a region of interest at least in part by processing the image and determine a pose of the region of interest; receive an identified region of interest and a pose of the identified region of interest from the region of interest model; and automatically provide instructions to a controller to adjust a pose of a surgical instrument relative to the pose of the identified region of interest.

Any of the aspects herein, wherein the image also depicts one or more trackers, and wherein the pose of the identified region of interest is determined relative to the one or more trackers.

Any of the aspects herein, wherein processing the image uses feature recognition to identify the region of interest.

Any of the aspects herein, wherein the surgical instrument comprises a robotic arm configured to orient an imaging device, and wherein the memory stores further data for processing by the processor that, when processed, causes the processor to provide instructions to a controller to adjust a pose of the robotic arm to frame all of the identified region of interest within a field of view of the imaging device.

Any of the aspects herein, wherein the memory stores further data for processing by the processor that, when processed, causes the processor to: receive an updated image, the updated image depicting the patient; input the updated image to the region of interest model; receive at least one of an updated identified region of interest and an updated pose of the updated identified region of interest; and automatically generate updated instructions for the controller to adjust the pose of the surgical instrument relative to the pose of the updated identified region of interest.

Any of the aspects herein, wherein the region of interest model is further trained using intraoperative patient data.

Any of the aspects herein, wherein the historical data comprises a plurality of images, at least some of the images depicting a region of interest similar to the identified region of interest.

A device for identifying a region of interest according to at least one embodiment of the present disclosure comprises at least one processor; and a memory storing data for processing by the processor, the data, when processed, causing the processor to: receive an image, the image depicting a patient; input the image to a region of interest model, wherein the region of interest model is trained using historical data and patient data received intraoperatively, and wherein the region of interest model is configured to identify a region of interest at least in part by processing the image and determine a pose of the region of interest; receive an identified region of interest and a pose of the identified region of interest from the region of interest model; and automatically generate instructions for a controller to adjust a pose of a robotic arm relative to the pose of the identified region of interest.

Any of the aspects herein, wherein processing the image comprises identifying a plurality of skeletal landmarks.

Any of the aspects herein, wherein the pose of the region of interest is determined relative to the plurality of skeletal landmarks.

Any of the aspects herein, wherein robotic arm orients an imaging device, and wherein the instructions cause the controller to move the robotic arm to orient the imaging device to frame all of the identified region of interest within a field of view of the imaging device.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10x Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

In surgical operations such as, for example, orthopedic surgery, a medical staff may use imaging to view an anatomy and a region of interest (ROI) of a patient. Identifying the ROI for surgery may be achieved based on a surgeon's anatomical knowledge, visual and tactile feedback from the surgeon, and often, use of X-ray, which exposes the patient to radiation.

At least one embodiment of the present disclosure uses artificial intelligence and depth cameras to identify the patient and the ROI. In some cases, a system may position X-ray components to target the ROI. In other cases, the system may identify an orientation and/or a position of a patient. In still other cases, the system may help identify patient movement. In other cases, the system may be used to identify the patient.

Embodiments of the present disclosure provide technical solutions to one or more of the problems of (1) automatically identifying a region of interest of a patient, (2) automatically positioning one or more components based on an identified region of interest, (3) monitoring movement of a patient, and (4) increasing patient safety.

Figure 1:
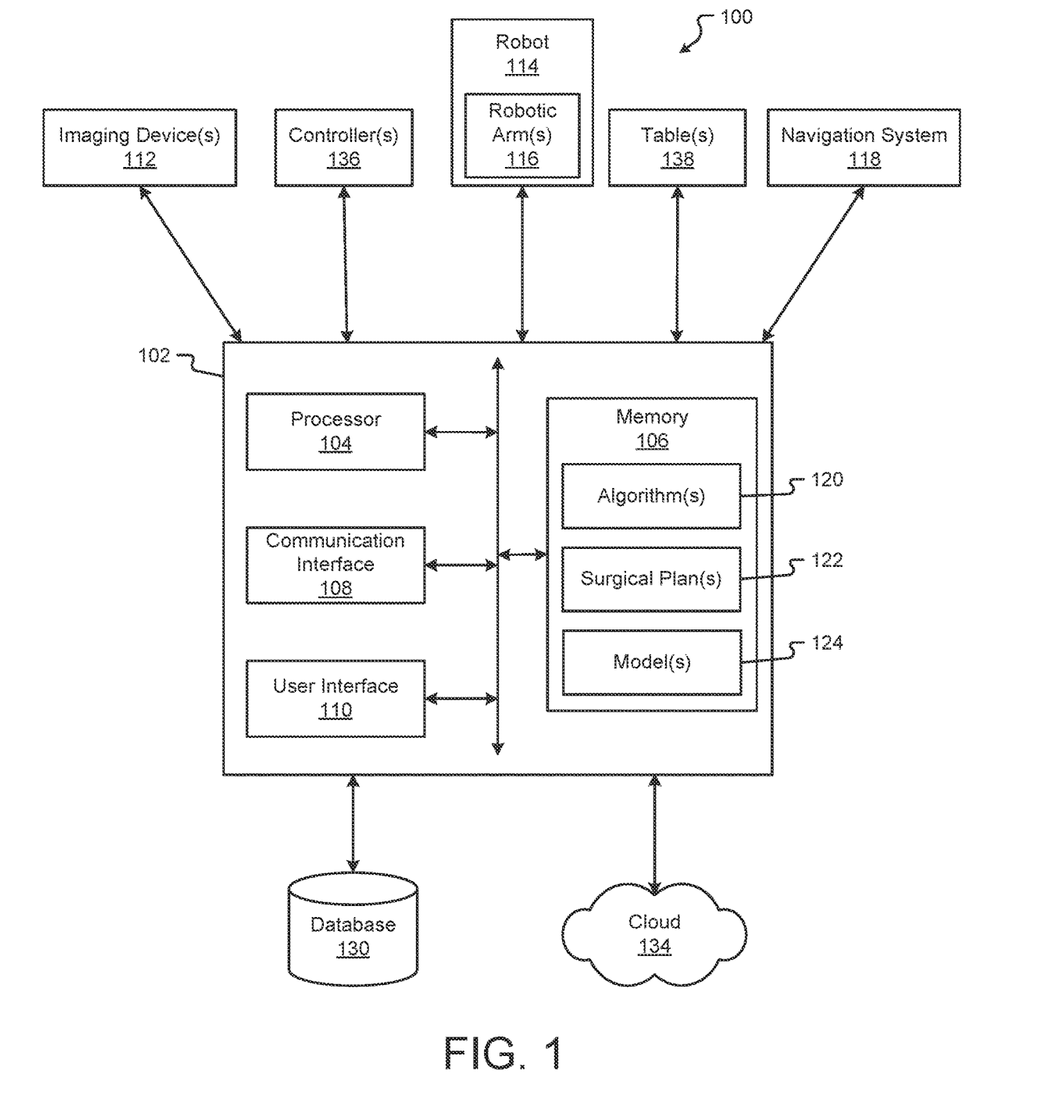
FIG. 1 is a block diagram of a system according to at least one embodiment of the present disclosure.

Turning first to FIG. 1, a block diagram of a system 100 according to at least one embodiment of the present disclosure is shown. The system 100 may be used to identify and locate a region of interest and/or carry out one or more other aspects of one or more of the methods disclosed herein. The system 100 comprises a computing device 102, one or more imaging devices 112, a robot 114, a navigation system 118, one or more controller(s) 136, one or more table(s) 138, a database 130, and/or a cloud or other network 134. Systems according to other embodiments of the present disclosure may comprise more or fewer components than the system 100. For example, the system 100 may not include the imaging device 112, the robot 114, the navigation system 118, the controller 136, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, the controller 136, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 400 and/or 500 described herein, or of any other methods. The memory 106 may store, for example, one or more algorithms 120, one or more surgical plan(s) 122, and/or one or more model(s) 124. Such instructions or algorithms may, in some embodiments, be organized into one or more applications, modules, packages, layers, or engines. Alternatively or additionally, the memory 106 may store other types of data (e.g., machine learning models, artificial neural networks, etc.) that can be processed by the processor 104 to carry out the various method and features described herein. Thus, although various components of memory 106 are described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the controller 136, the database 130, and/or the cloud 134.

The computing device 102 may also comprise a communication interface 108. The communication interface 108 may be used for receiving image data or other information from an external source (such as the imaging device 112, the robot 114, the navigation system 118, the controller 136, the database 130, the cloud 134, and/or any other system or component not part of the system 100), and/or for transmitting instructions, images, or other information to an external system or device (e.g., another computing device 102, the imaging device 112, the robot 114, the navigation system 118, the controller 136, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image an operating room, one or more objects, a patient, anatomical feature(s) (e.g., a bone, veins, tissue, etc.) and/or other aspects of patient anatomy to yield image data. "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, a depth camera, a stereo camera, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers or trackers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

In the illustrated embodiment, the system 100 includes the controller 136, though in some embodiments the system 100 may not include the controller 136. The controller 136 may be integrated with any component of the system 100 such as, for example, the robot 114 and/or the table 138, though the controller 136 may be separate from the robot 114 and/or the table 138. The controller 136 may be an electronic, a mechanical, or an electro-mechanical controller. The controller 136 may comprise or may be any processor described herein. The controller 136 may comprise a memory storing instructions for executing any of the functions or methods described herein as being carried out by the controller 136. In some embodiments, the controller 136 may be configured to simply convert signals received from the computing device 102 (e.g., via a communication interface 108) into commands for operating the navigation system 118, the robot 114, and/or the robotic arm 116. In other embodiments, the controller 136 may be configured to process and/or convert signals received from the navigation system 118, the robot 114, and/or the robotic arm 116. Further, the controller 136 may receive signals from one or more sources (e.g., the navigation system 118, the robot 114, and/or the robotic arm 116) and may output signals to one or more sources.

The table 138 may be any operating table configured to support a patient during a surgical procedure. The table 138 may include any accessories mounted to or otherwise coupled to the table 138 such as, for example, a bed rail, a bed rail adaptor, an arm rest, an extender, or the like. The table 138 may be stationary or may be operable to maneuver a patient (e.g., the table 138 may be able to move). In some embodiments, the table 138 may include one or more motors operable to move the table 138 or to move at least a portion of the table 138. The one or more motors may be operated automatically by, for example, the controller 136. In other instances, the one or more motors may be operated based on input received from a user. In some embodiments, the table 138 and the robotic arm 116 may operate in the same coordinate system.

In some embodiments, the table 138 has two positioning degrees of freedom and one rotational degree of freedom, which allows positioning of the specific anatomy of the patient anywhere in space (within a volume defined by the limits of movement of the table 138). For example, the table 138 can slide forward and backward and from side to side, and can tilt (e.g., around an axis positioned between the head and foot of the table 138, and extending from one side of the table 138 to the other) and/or roll (e.g., around an axis positioned between the two sides of the table 138, and extending from the head of the table 138 to the foot thereof). In other embodiments, the table 138 can bend at one or more areas (which bending may be possible due to, for example, the use of a flexible surface for the table 138, or by physically separating one portion of the table 138 from another portion of the table 138 and moving the two portions independently). In at least some embodiments, the table 138 may be manually moved or manipulated by, for example, a surgeon or other user, or the table 138 may comprise one or more motors, actuators, and/or other mechanisms configured to enable movement and/or manipulation of the table 138 by a processor such as the processor 104.

The database 130 may store information that correlates one coordinate system to another (e.g., one or more robotic coordinate systems to a patient coordinate system and/or to a navigation coordinate system). The database 130 may additionally or alternatively store, for example, one or more surgical plans 122 (including, for example, image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the methods 400 and/or 500 described herein. The system 100 or similar systems may also be used for other purposes.

Figure 2:
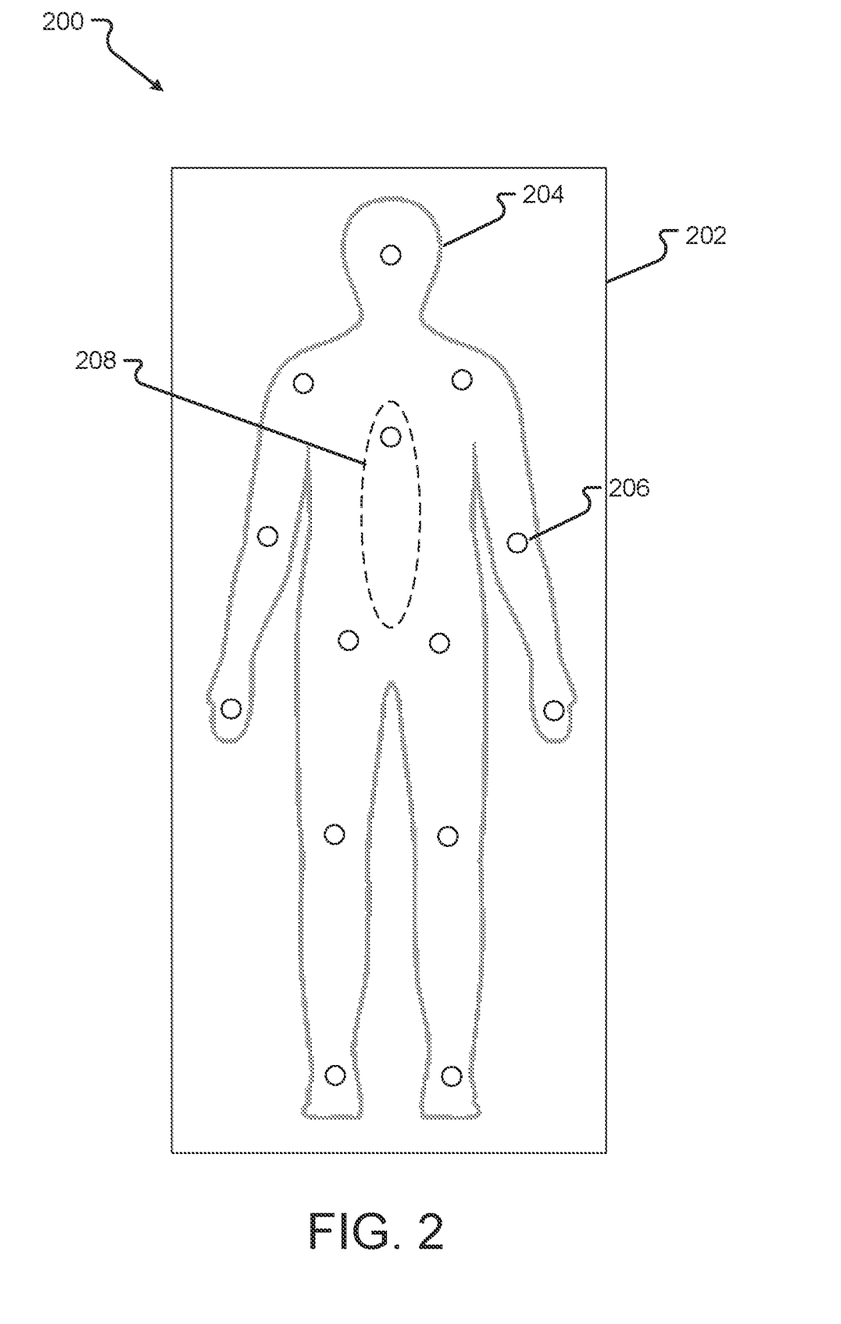
FIG. 2 is a schematic drawing of a plurality of skeletal landmarks according to at least one embodiment of the present disclosure.
Figure 3:
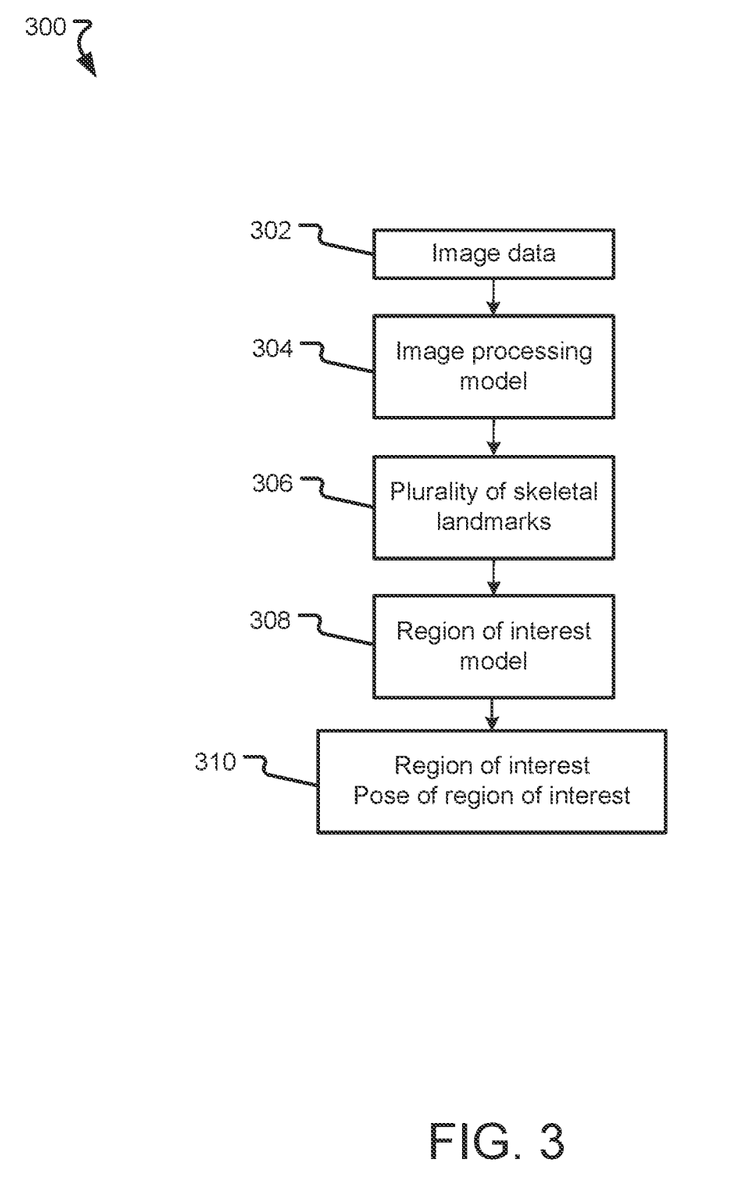
FIG. 3 is a flowchart according to at least one embodiment of the present disclosure.

Turning to FIGS. 2 and 3, an example image 200 of a patient 204 in a supine position on a table 202 and an example of a model architecture 300 that supports methods and systems (e.g., Artificial Intelligence (AI)-based methods and/or system) for identifying and locating a region of interest are shown, respectively. FIGS. 1 to 3 will now be described with respect to certain non-limiting examples.

Prior to a start of a surgical procedure, image data 302 of the patient 204 may be obtained by the imaging device 112 (or a different imaging device), which may be, for example, a depth camera. The image data 302 may be processed by the processor 104 using one or more models 124 such as, for example, an image processing model 304, to identify a plurality of skeletal landmarks 206 (shown in FIG. 2 as spheres), 306 (shown in FIG. 3). It will be appreciated that the plurality of skeletal landmarks 206 are shown as spheres in FIG. 2 for illustrative purposes, though in some instances the plurality of skeletal landmarks 206 may be displayed or depicted as spheres, or any other shape, on the user interface 110. The plurality of skeletal landmarks 206, 306 may include any number of landmarks. The plurality of skeletal landmarks 206, 306 may include, for example, one or more landmarks for a skull, a spine, one or more limbs, a torso, or any other portion of the patient 204.

In some embodiments the image data 302 may depict some or all of the patient 204. In such embodiments, the image processing model 304 may be trained using one or more sets of historical image data, wherein at least some sets of historical image data may contain a plurality of known skeletal landmarks of a different, historical patient. In other embodiments, the image data may depict the patient 204 and one or more trackers. In such embodiments, the image processing model 304 may be trained using one or more sets of historical image data, wherein at least some sets of historical image data may depict a historical patient, one or more trackers, and a plurality of known skeletal landmarks relative to the one or more trackers. The image processing model 304 may be configured to identify a plurality of skeletal landmarks 206, 306, regardless of which historical datasets are used to train the model 304.

The image processing model 304 may output the plurality of skeletal landmarks 206, 306. The plurality of skeletal landmarks 206, 306 may be used by the processor 104 as input for a region of interest model 308. The region of interest model 308 may identify a region of interest 208 (depicted in FIG. 2 as a dashed oval), 310 and determine a pose of the region of interest 208, 310. It will be appreciated that the region of interest 208 is shown as a dashed oval in FIG. 2 for illustrative purposes, though in some instances the region of interest 208 may be displayed as a dashed oval, or any other shape and/or line style, on the user interface 110. The region of interest 208, 310 may be, for example, a spinal region, one or more anatomical elements, a collection of multiple anatomical elements, or any portion of the patient 204. In some embodiments, the region of interest model 308 may be configured to determine a pose of the patient 204 based on the plurality of skeletal landmarks 206, 306. The region of interest model 308 may also be configured to identify the region of interest 208, 310 and/or the pose of the identified region of interest based on the determined pose of the patient 204 and/or the plurality of skeletal landmarks 206, 306. In some embodiments, the region of interest model 308 is configured to identify the region of interest 208, 310 relative to the plurality of skeletal landmarks 206, 306.

Identifying the region of interest 208, 310 may include identifying a boundary, a volume, and/or a shape of the region of interest 208, 310. The region of interest model 308 may be trained to identify the region of interest 208, 310 using one or more historical datasets. Each historical dataset may be, for example, an image (whether 3D, 2D, or a combination of both) of a region of interest (whether a spinal region, an anatomical element, or any portion of a patient) in a historical patient. In some instances, the region of interest model 308 may be trained using a combination of one or more historical datasets and current patient data. The current patient data may be, for example, the image data 302. It will be appreciated that during a surgical procedure, current patient data (e.g., image data 302) may be inputted to the region of interest model 308 in real-time and the region of interest model 308 may use the current patient data as training data to improve the model 308 in real-time.

The region of interest model 308 may output the region of interest 208, 310 and the pose of the region of interest. The region of interest 208, 310 and the pose of the region of interest may be used to generate instructions to control a surgical instrument which may be, for example, the robotic arm 116 and/or the table 138, 202, as will be described with respect to FIGS. 4 and 5 below.

In some embodiments, the plurality of skeletal landmarks 206, 306 and/or the region of interest 308, 310 may be displayed on, for example, the user interface 110. In some instances, a user such as, for example, a surgeon or other medical provider, may provide input to adjust the plurality of skeletal landmarks 206, 306 and/or the region of interest 308, 310.

Figure 4:
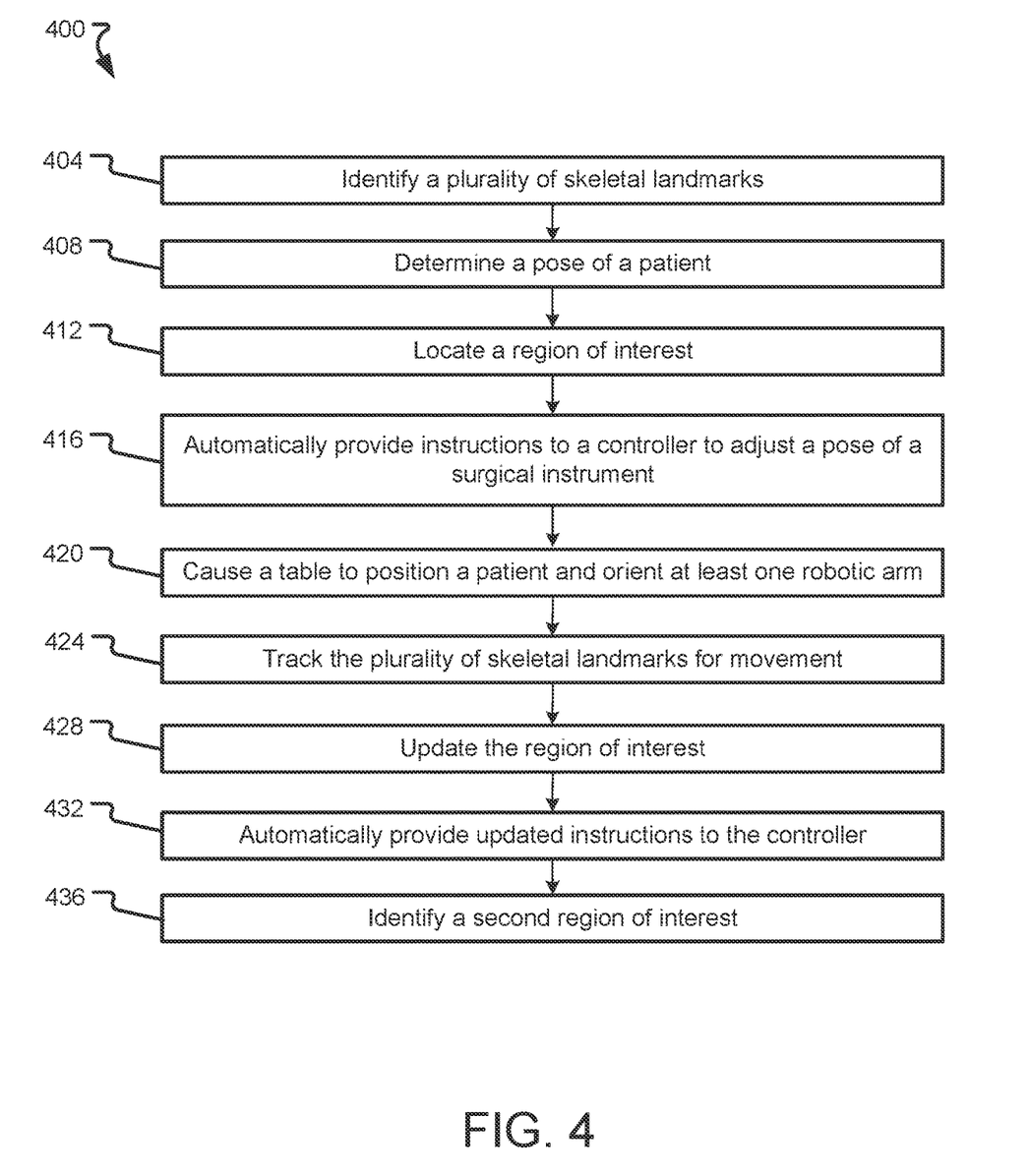
FIG. 4 is a flowchart according to at least one embodiment of the present disclosure.

FIG. 4 depicts a method 400 that may be used, for example, identifying a region of interest.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing instructions stored in a memory such as the memory 106. The instructions may correspond to one or more steps of the method 400 described below. The instructions may cause the processor to execute one or more algorithms, such as the algorithm 120.

The method 400 comprises identifying a plurality of skeletal landmarks (step 404). The plurality of skeletal landmarks may be the same as or similar to the plurality of skeletal landmarks 206, 306. The plurality of skeletal landmarks may include, for example, one or more landmarks for a skull, a spine, one or more limbs, a torso, or any other portion of a patient. A processor such as the processor 104 may use an image processing model such as the image processing model 304 to identify the plurality of skeletal landmarks in image data received from an imaging device such as the imaging device 112. The image processing model 304 may be trained using historical data sets where at least some data sets comprise image data and a known plurality of skeletal landmarks of a historical patient.

In some embodiments, the image data may depict a patient and the one or more skeletal landmarks may be identified relative to the patient. In other embodiments, the image data may depict one or more trackers and the plurality of skeletal landmarks may be identified relative to the one or more trackers. The plurality of skeletal landmarks may be displayed on, for example, a user interface such as the user interface 110. In some instances, a user such as, for example, a surgeon or other medical provider, may adjust the plurality of skeletal landmarks.

The method 400 also comprises determining a pose of a patient (step 408). The pose of the patient may be determined based on the plurality of skeletal landmarks. Each skeletal landmark may include a position and/or orientation information for each landmark, which may be used to determine the pose of the patient. For example, a first set of skeletal landmarks may correspond to a skull of a patient and a second set of skeletal landmarks may correspond to two legs of the patient. Thus, at least a pose of the skull, or head, of the patient and a pose of each leg of the patient may be determined from the first set and the second set of skeletal landmarks.

The method 400 also comprises locating a region of interest (step 412). Locating the region of interest may be based on the determined pose. More specifically, the region of interest may be located relative to the determined pose of the patient. For example, if patient is laying prone on a table such as the table 138, 202 and the region of interest is a spinal region, the spinal region may be located along, for example, at least a portion of a back of the patient. A pose of the region of interest may also be determined based on the pose of the patient.

In some embodiments, the region of interest may be located relative to the plurality of skeletal landmarks. In such embodiments, the step 408 may be omitted. It will also be appreciated that the region of interest may be located relative to the plurality of skeletal landmarks and the pose of the patient. In embodiments where the image depicts one or more trackers, the region of interest may be located relative to one or more trackers.

Figure 5:
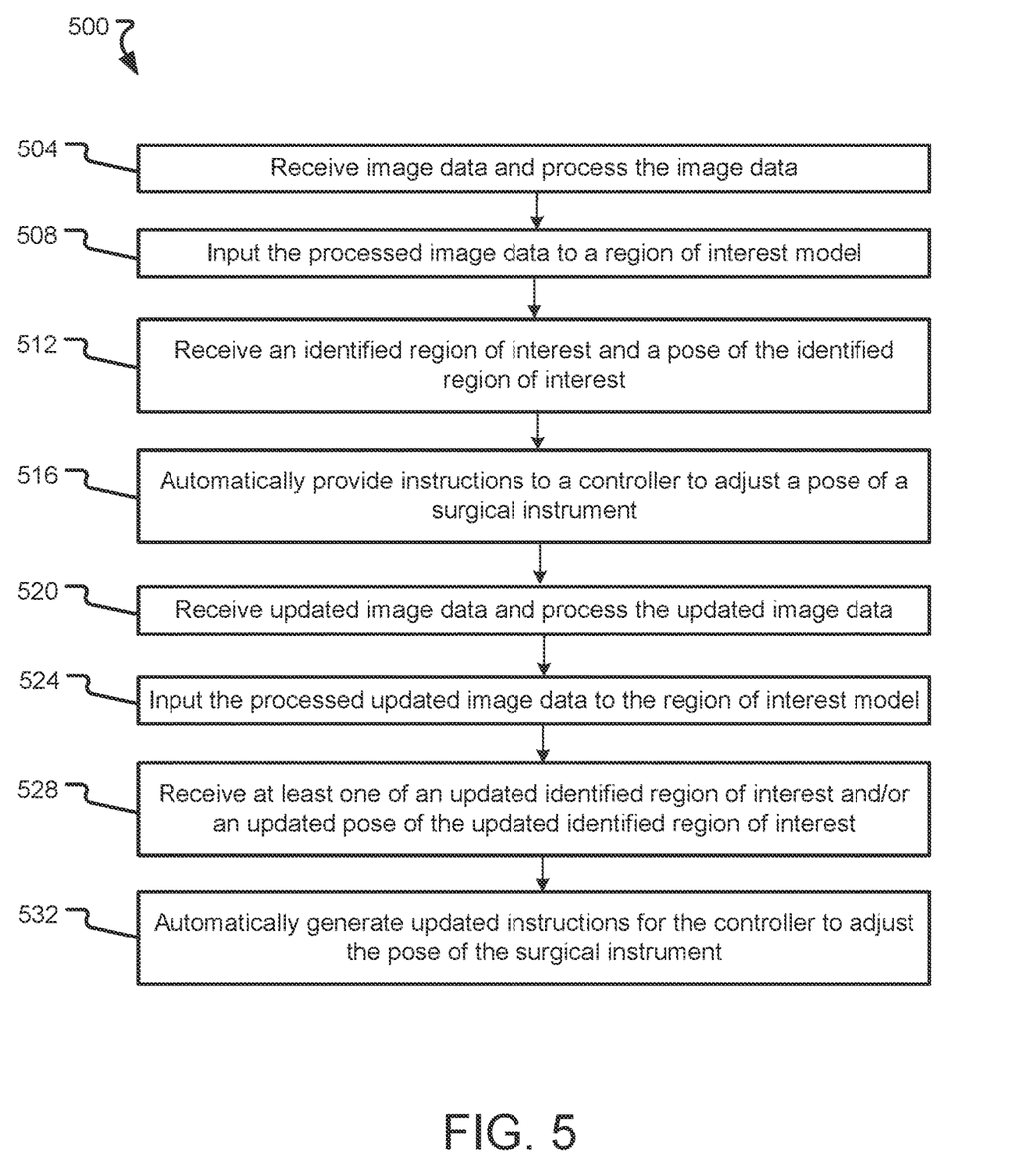
FIG. 5 is a flowchart according to at least one embodiment of the present disclosure.

In some embodiments, locating the region of interest may comprise identifying the region of interest (whether through image processing or otherwise and discussed in detail with respect to step 508 of method 500 below) and/or determining a pose of the region of interest (also discussed in detail with respect to step 508 of method 500).

The method 400 also comprises automatically providing instructions to a controller to adjust a pose of a surgical instrument (step 416). The controller may be the same as or similar to the controller 136. The instructions may be generated automatically by, for example, the processor and transmitted to the controller. The instructions may cause the controller to adjust the pose of the surgical instrument relative to the identified region of interest.

The method 400 also comprises providing instructions to cause a table to position a patient and orient at least one robotic arm (step 420). The table may be the same as or similar to the table 138, 202 and in some embodiments, the surgical instrument may be a robotic arm such as the robotic arm 116. The robotic arm may, for example, orient a tool, an instrument, and/or an imaging device. In embodiments where the robotic arm orients an imaging device, the instructions may, for example, cause the controller to cause the robotic arm to orient the imaging device to frame all of the identified region of interest within a field of view of the imaging device.

In some embodiments, the instructions may cause the table to position the patient and orient the at least one robotic arm relative to the identified region of interest. For example, the identified region of interest may be a spinal region and the instructions may cause the controller to cause the table to position the patient so that the spinal region is within reach of the robotic arm and cause the robotic arm to orient, for example, a tool at the spinal region.

The method 400 also comprises tracking the plurality of skeletal landmarks for movement (step 424). During a surgical procedure, the plurality of skeletal landmarks may be tracked for movement whether due to movement of the patient, movement of the table, and/or a change to the region of interest due to the surgical procedure (e.g., movement of the spine). Movement of one or more skeletal landmarks may indicate that the region of interest may have also moved and/or may have changed (whether in volume, shape, or both).

Tracking the plurality of skeletal landmarks may comprise receiving a first image taken at a first timeframe from the imaging device and identifying the plurality of skeletal landmarks as described above with respect to step 404. Tracking the plurality of skeletal landmarks may also comprise receiving a second image taken at a second timeframe from the imaging device. A processor such as the processor 104 may compare the first image to the second image to determine if any skeletal landmark has moved. In some embodiments, movement of some skeletal landmarks may not affect the region of interest. As such, the detected movement may not trigger step 428 below. In some embodiments, such movement may simply alert a user. In other embodiments, where movement of one or more skeletal landmarks may affect the region of interest, step 428, described below, may occur.

The method 400 also comprises updating the region of interest (step 428). The step 428 may be the same as or similar to the step 412. In some embodiments, updating the region of interest may include updating a shape, a volume, or a size of the region of interest. In other embodiments, updating the region of interest may include updating a pose of the region of interest. In still other embodiments, updating the region of interest may include updating the shape, the volume, or the size of the region of interest and the pose of the region of interest.

The method 400 also comprises automatically provide updated instructions to the controller to adjust the pose of the surgical instrument (step 432). The pose of the surgical instrument may be adjusted relative to the updated region of interest. The step 432 may be the same as or similar to the step 416.

It will be appreciated that steps 424-432 may be repeated any number of times. For example, steps 428 and 432 may be repeated any time movement of a skeletal landmark is detected. Further, step 424 may be continuously executed throughout a surgical procedure. In other instances, step 424 may be executed upon input from a user. For example, prior to a surgical task, a user such as, for example, a surgeon may check if movement has occurred by executing step 424.

The method 400 also comprises locating a second region of interest (step 436). The method 400 may or may not include step 436. In embodiments where the method 400 includes the step 436, the region of interest located in step 412 may be a first region of interest located at a first timeframe and the second region of interest may be located at a second timeframe. In some embodiments, the first timeframe may be the same as the second timeframe. In other words, the first region of interest may be identified at the same time as the second region of interest. For example, the first region of interest may be a surgical site and the second region of interest may be a site next to the surgical site that is monitored for, for example, potential contact from a surgical instrument used to perform a task at the surgical site. In other instances, the first timeframe may be prior to the second timeframe. For example, the first region of interest may be an incision site and the second region of interest may be a portion of the patient accessible through the incision site that is located after the incision is formed.

The first region of interest may also have a pose, size, shape, and/or volume different from a pose, size, shape, and/or volume of the second region of interest. In other embodiments, the first region of interest may have a pose, size, shape, and/or volume the same as a pose, size, shape, and/or volume of the second region of interest.

It will be appreciated that step 436 may be repeated for any number of regions of interest. It will also be appreciated that multiple regions of interest may be identified at the same timeframe or may be identified at different timeframes.

The present disclosure encompasses embodiments of the method 400 that comprise more or fewer steps than those described above, and/or one or more steps that are different than the steps described above.

FIG. 5 depicts a method 500 that may be used, for example, identifying a region of interest.

The method 500 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 500. The at least one processor may perform the method 500 by executing instructions stored in a memory such as the memory 105. The instructions may correspond to one or more steps of the method 500 described below. The instructions may cause the processor to execute one or more algorithms, such as the algorithm 120.

The method 500 comprises receiving image data and processing the image data (step 504). The image data may be received or obtained from an imaging device such as the imaging device 112, which may be any imaging device such as a camera, a depth camera, X-ray based imaging device, or ultrasound imaging device. The image data may comprise one or more 2D images, one or more 3D images, or a combination of one or more 2D images and one or more 3D images. In some embodiments, one imaging device may be used to obtain the image data. In other embodiments, multiple imaging devices may be used to obtain the image data. In examples wherein more than one image is received or multiple images are used to construct a 3D model, a first imaging device may obtain a first one of the images independently of a second imaging device obtaining a second one of the images. In another example, at least a first one of the images may be obtained with a first imaging device and at least a second one of the images may be obtained with a second imaging device. In other embodiments, the image may be received via a user interface such as the user interface 110 and/or via a communication interface such as the communication interface 108 of a computing device such as the computing device 102, and may be stored in a memory such as the memory 105. The image data may also be generated by and/or uploaded to any other component of the system 100. In some embodiments, the image may be indirectly received via any other component of the system 100 or a node of a network to which the system 100 is connected.

The image data may depict a surgical operating room, a patient, one or more objects, one or more tools, one or more instruments, and/or one or more users such as a surgeon and/or other medical providers. In some embodiments, the image data may also depict one or more trackers. The image data may be processed by a processor such as the processor 104 using one or more models such as, for example, an image processing model 304, to identify a plurality of skeletal landmarks such as the plurality of skeletal landmarks 206, 306. The image processing model may be trained using one or more sets of historical image data, wherein at least some sets of historical image data may contain a plurality of known skeletal landmarks of a different patient. In other embodiments, the image processing model may be trained using one or more sets of historical image data, wherein at least some sets of historical image data may depict a patient, one or more trackers, and a plurality of known skeletal landmarks relative to the one or more trackers.

The method 500 also comprises inputting the processed image data to a region of interest model (step 508). The processed image data may comprise the plurality of skeletal landmarks. The region of interest model may be the same as or similar to the region of interest model 308. The region of interest model may be configured to identify a region of interest such as the region of interest 208, 310 and determine a pose of the region of interest. The region of interest may be, for example, a spinal region, one or more anatomical elements, or any portion of the patient. In some embodiments, the region of interest model may determine a pose of the patient based on the plurality of skeletal landmarks. The region of interest model may also be configured to identify the region of interest and/or the pose of the identified region of interest based on a pose of the patient determined from the plurality of skeletal landmarks.

Identifying the region of interest may include identifying a boundary, a volume, and/or a shape of the region of interest. The region of interest model may be trained to identify the region of interest using one or more historical datasets. Each historical dataset may be, for example, an image (whether 3D, 2D, or a combination of both) of a region of interest (whether a spinal region, an anatomical element, or any portion of a patient) in a historical patient. In some instances, the region of interest model may be trained using a combination of one or more historical datasets and current patient data. The current patient data may be, for example, the image data. It will be appreciated that during a surgical procedure, current patient data (e.g., image data) may be inputted to the region of interest model in real-time and the region of interest model may use the current patient data as training data to improve the model in real-time.

The region of interest model may output an identified region of interest and a pose of the identified region of interest.

The method 500 also comprises receiving an identified region of interest and a pose of the identified region of interest (step 512). The identified region of interest and the pose of the identified region of interest may be obtained from, for example, step 508 described above. In some embodiments, the identified region of interest and/or the pose of the identified region of interest may be adjusted by a user such as, for example, a surgeon or other medical provider. For example, the surgeon may adjust a boundary, a size, a shape, or a pose of the region of the interest.

The method 500 also comprises automatically providing instructions to a controller to adjust a pose of a surgical instrument (step 516). The step 516 may be the same as or similar to the step 416 of method 400.

The method 500 also comprises receiving updated image data. (step 520). The step 520 may be the same as or similar to the step 504. Receiving the updated image data may comprise comparing the updated image data to the image data received in step 504. A change in the updated image data may indicate that movement of the patient, the bed, and/or the region of interest may have occurred.

The method 500 also comprises inputting the updated image to the region of interest model (step 524). The step 524 may be the same as or similar to the step 508.

The method 500 also comprises receiving at least one of an updated identified region of interest and/or an updated pose of the updated identified region of interest (step 528). The step 528 may be the same as or similar to the step 512. In some embodiments, an updated identified region of interest may be received in which a size, a boundary, a volume, and/or a shape of the identified region of interest is updated. In other embodiments, the identified region of interest may remain the same and an updated pose of the identified region of interest may be received. In still other embodiments, an updated identified region of region in which a size, a boundary, a volume, and/or a shape of the identified region of interest is updated and an updated pose of the updated identified region of interest may be both received.

The method 500 also comprises automatically generating updated instructions for the controller to adjust the pose of the surgical instrument (step 532). The pose of the surgical instrument may be adjusted relative to the updated identified region of interest and/or the updated pose of the updated identified region of interest. The step 532 may be the same as or similar to the step 516.

It will be appreciated that steps 520-532 may be repeated any number of times. For example, steps 524-532 may be repeated when updated image data is received that is different from the initial image data. Further, step 520 may be continuously executed throughout a surgical procedure. In other instances, step 520 may be executed upon input from a user. For example, prior to a surgical task, a user such as, for example, a surgeon may confirm that no change has occurred by executing step 520.

The present disclosure encompasses embodiments of the method 500 that comprise more or fewer steps than those described above, and/or one or more steps that are different than the steps described above.

As noted above, the present disclosure encompasses methods with fewer than all of the steps identified in FIGS. 4 and 5 (and the corresponding description of the methods 400 and 500), as well as methods that include additional steps beyond those identified in FIGS. 4 and 5 (and the corresponding description of the methods 400 and 500). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for identifying a region of interest comprising:
   an imaging device;
   a controller;
   at least one processor; and
   a memory storing data for processing by the processor, the data, when processed, causing the processor to:
     identify a plurality of skeletal landmarks from an image received from the imaging device;
     determine a pose of a patient based on the plurality of skeletal landmarks;
     identify a region of interest on the patient based on the determined pose;
     automatically provide instructions to the controller to adjust a pose of a surgical instrument relative to the region of interest;
     track the plurality of skeletal landmarks for movement; and
     update the region of interest when movement of the plurality of skeletal landmarks is detected.

2. The system of claim 1, wherein the imaging device comprises a depth camera.

3. The system of claim 1, wherein the memory stores further data for processing by the processor that, when processed, causes the processor to automatically provide updated instructions to the controller that adjusts the pose of the surgical instrument relative to the updated region of interest.

4. The system of claim 1, wherein the region of interest comprises a spinal region.

5. The system of claim 1, wherein the region of interest is identified relative to the plurality of skeletal landmarks.

6. The system of claim 1, wherein the surgical instrument comprises at least one robotic arm.

7. The system of claim 6, further comprising a table on which the patient is positioned, and wherein the memory stores further data for processing by the processor that, when processed, causes the processor to cause the table to position the patient and orient the at least one robotic arm based on the region of interest.

8. The system of claim 7, wherein the at least one robotic arm and the table operate in a common coordinate space.

9. The system of claim 1, wherein the region of interest is a first region of interest, and wherein the memory stores further data for processing by the processor that, when processed, causes the processor to:
   identify a second region of interest, wherein the first region of interest is identified at a time stamp prior to a time stamp of the second region of interest, and the first region of interest has a pose different from a pose of the second region of interest.

* * * * *